United States Patent
Steinecker

(10) Patent No.: US 8,968,560 B2
(45) Date of Patent: Mar. 3, 2015

(54) CHROMATOGRAPHY USING MULTIPLE DETECTORS

(75) Inventor: William H. Steinecker, Dedham, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 2031 days.

(21) Appl. No.: 11/951,495

(22) Filed: Dec. 6, 2007

(65) Prior Publication Data
US 2009/0150087 A1 Jun. 11, 2009

(51) Int. Cl.
G01N 30/46 (2006.01)
G01N 30/86 (2006.01)
G01N 30/78 (2006.01)

(52) U.S. Cl.
CPC .......... *G01N 30/461* (2013.01); *G01N 30/8624* (2013.01); *G01N 30/78* (2013.01)
USPC ................ 210/198.2; 210/656; 95/82; 95/86; 96/101; 96/104; 422/70; 422/89

(58) Field of Classification Search
CPC .. G01N 30/461; G01N 30/8624; G01N 30/78
USPC ............. 210/635, 656, 659, 198.2; 95/82, 86; 96/101, 104; 422/70, 89
See application file for complete search history.

(56) References Cited

U.S. PATENT DOCUMENTS

| | | | |
|---|---|---|---|
| 3,097,518 A * | 7/1963 | Taylor | 73/23.4 |
| 3,141,323 A | 7/1964 | Taylor et al. | |
| 3,263,488 A | 8/1966 | Martin | |
| 4,199,323 A * | 4/1980 | Miller et al. | 210/198.2 |
| 4,909,078 A | 3/1990 | Sittler et al. | |
| 4,935,145 A | 6/1990 | Cortes et al. | |
| 5,004,538 A * | 4/1991 | Apfel | 210/198.2 |
| 5,104,221 A * | 4/1992 | Bott et al. | 356/336 |
| 5,114,551 A * | 5/1992 | Hjerten et al. | 204/452 |

(Continued)

FOREIGN PATENT DOCUMENTS

| | | |
|---|---|---|
| DE | 19808213 A1 | 2/1998 |
| DE | 19808213 A1 | 9/1999 |

(Continued)

OTHER PUBLICATIONS

Cruz et al., Microfabricated thermal conductivity detector for the micro-ChemLabTM, Sensors and Actuators B, 2007, vol. 121, pp. 414-422.

(Continued)

*Primary Examiner* — Ernest G Therkorn

(57) ABSTRACT

Methods and related apparatuses and mixtures are described for chromatographic analysis. The described system includes a pressurized source of a mobile phase and a flow path in fluid communication with the pressurized source such that the mobile phase flows through the flow path. The system also includes an injector in fluid communication with the flow path and downstream of the pressurized source, the injector being configured to inject a sample into the flow path. A first column located downstream of the injector, contains a stationary phase, and forms part of the flow path. A first detector is positioned to detect properties of fluid in the flow path at a location downstream of the injector and upstream from the first column. A second detector is positioned to detect properties of fluid in the flow path at a location downstream of the first column.

14 Claims, 3 Drawing Sheets

(56) References Cited

U.S. PATENT DOCUMENTS

| | | | |
|---|---|---|---|
| 5,436,166 A * | 7/1995 | Ito et al. | 436/161 |
| 5,756,878 A | 5/1998 | Muto et al. | |
| 5,922,184 A * | 7/1999 | Binder et al. | 204/452 |
| 6,344,172 B1 * | 2/2002 | Afeyan et al. | 422/70 |
| 6,702,989 B2 | 3/2004 | Sacks et al. | |
| 7,202,471 B2 * | 4/2007 | Hondo et al. | 250/281 |
| 2002/0121468 A1 * | 9/2002 | Fischer et al. | 210/198.2 |
| 2004/0083788 A1 * | 5/2004 | Mueller | 73/23.36 |
| 2004/0099046 A1 * | 5/2004 | Mueller | 73/23.4 |
| 2005/0123452 A1 | 6/2005 | Mueller et al. | |
| 2007/0181505 A1 * | 8/2007 | DeMarco | 210/656 |

FOREIGN PATENT DOCUMENTS

| | | |
|---|---|---|
| DE | 10064138 A1 | 7/2002 |
| DE | 10105728 A1 | 9/2002 |
| DE | 10064138 B4 | 2/2004 |
| DE | 10105728 B4 | 9/2005 |
| EP | 0654667 A1 | 8/1994 |
| WO | 9714957 A1 | 4/1997 |
| WO | 0250530 A2 | 6/2002 |
| WO | 03083467 A2 | 9/2003 |
| WO | 2008067296 A2 | 6/2008 |

OTHER PUBLICATIONS

Kimura et al., Application of the air-bridge microheater to gas detection, Sensors and Actuators B, 1995, vol. 24-25, pp. 857-860.

Chen et al, Thermal analysis and simulation of the microchannel flow in miniature thermal conductivity detectors, Sensors and Actuators, 2000, vol. 79, pp. 211-218.

Gajda et al., Applications of thermal silicon sensors on membranes, Sensors and Actuators A, 1995, vol. 49, pp. 1-9.

Laugere et al., Downscaling aspects of a conductivity detector for application in on-chip capillary electrophoresis, Sensors and Actuators A, 2001, vol. 92, pp. 109-114.

Simon et al., Thermal and gas-sensing properties of a micromachined thermal conductivity sensor for the detection of hydrogen in automotive applications, Sensors and Actuators A, 2002, vol. 97-98, pp. 104-108.

Sorge, Fully integrated thermal conductivity sensor for gas chromatography without dead volume, Sensors and Actuators A, 1997, vol. 63, pp. 193-195.

Wu et al., Fabrication and characterization of thermal conductivity detectors (TCDs) of different flow channel and heater designs, Sensors and Actuators A, 2002, vol. 100, pp. 37-45.

PCT/US2008/078066, International Search Report and Written Opinion, dated Mar. 5, 2009, 19 pages.

* cited by examiner

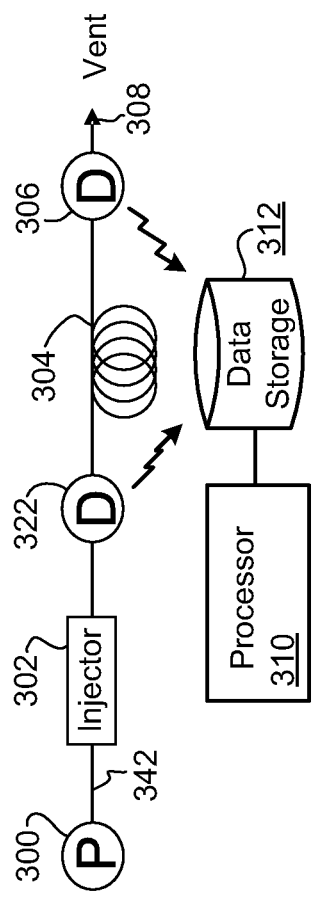
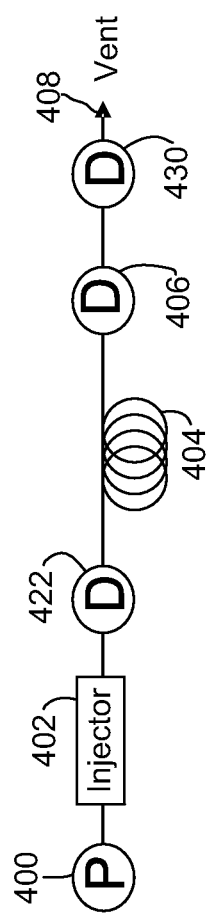
Fig. 3
Fig. 4

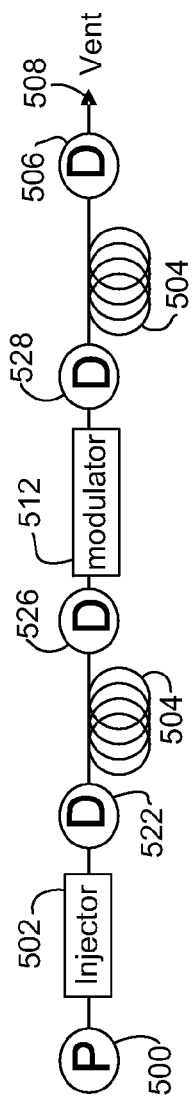
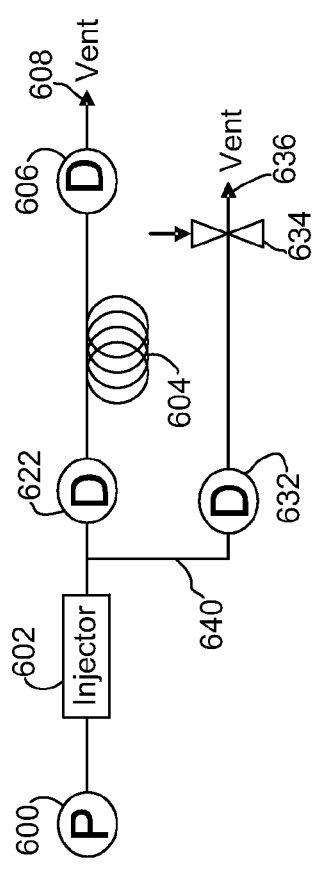
Fig. 5
Fig. 6

CHROMATOGRAPHY USING MULTIPLE DETECTORS

BACKGROUND OF THE INVENTION

1. Field of the Invention

This patent specification relates to Chromatography. More particularly, this patent specification relates to systems and methods for gas chromatography.

2. Background of the Invention

Chromatography is the field of separating chemicals based on differences in properties such as volatility, absorption, adsorption, size, etc. In this field, different rates of migration along a given flow path (gas, liquid, supercritical fluid, etc) result in the spatial separation of chemical analytes. This differential migration is achieved by differing rates of interaction with the separation column or by different values of analyte mobility. FIG. 1 shows the configuration of a typical conventional gas chromatography system. As shown the configuration includes a pressure source 100, injector 102, a column 104, a detector 106 and vent 108. The injector 102 provides a sharp pulse of the sample (chemical mixture) into the system flow path. The column 104 provides the physical separation, and the detector detects analytes as they elute from the column. Some configurations employ other elements such as a focuser 110, modulator 112, and an additional column 114 to enhance performance or provide otherwise unattainable separations.

Modern chromatography has evolved substantially; many examples exist of advanced methods with various non-standard devices that perform a variety of tasks that provide enhanced chromatographic performance and/or analyte information, as well as hyphenated methods that bridge existing standards and protocols. Such devices include cryogenic focusers, adsorbent based preconcentrators, and band enhancement devices (similar to a focuser). Adding to this complexity are two-dimensional methods that use modulators to control injection into second columns in attempt to measure a second, independent retention time. Also of great significance is the integration of microfabricated devices and systems with traditional chromatographic systems. Microfluidics offer many advantages, but also have the potential for adding new sources of band broadening and other analytical errors. A growing problem common to these relatively recent methods and devices is how to diagnose problems within the system. To achieve the best separation performance, it is necessary to provide injections that are small with respect to the band broadening that will occur on the column. However, with the expected day to day changes in system elements, such as the devices mentioned above, the injection profile could easily change.

Quantitative analysis is typically based on comparison of the observed peak areas to the injected quantity of sample. This can result in a significant error if the sample volume varies (e.g. syringe error) or some injected components do not actually flow from the injector to the column (or between succeeding devices in the flow path).

U.S. Patent Application Publication No. US2005/0123452A1 discloses a chromatograph for analyzing natural gas having non-destructive detectors placed between columns in a multi-column combination. However, these detectors are used for detecting elutes from earlier columns that are discharged prior to a later column having a molecular sieve, so as not to contaminate the sieve. The detectors are not used for diagnosis of problems within the system. A detector is also disclosed in location before the first column. However, this detector is only used during a back-flushing operation where the detector can then detect eluents from the first column.

SUMMARY OF THE INVENTION

According to embodiments, a system for chromatographic analysis of a sample containing a plurality of components is provided. The system includes a pressurized source of a mobile phase and a flow path in fluid communication with the pressurized source such that the mobile phase flows through the flow path. The system also includes an injector in fluid communication with the flow path and downstream of the pressurized source, the injector being configured to inject a sample into the flow path. A first column located downstream of the injector, contains a stationary phase, and forms part of the flow path. A first detector is positioned to detect properties of fluid in the flow path at a location downstream of the injector and upstream from the first column. A second detector is positioned to detect properties of fluid in the flow path at a location downstream of the first column. A processor is configured to receive first measurement data from the first detector and second measurement data from the second detector and combine the first and second measurement data to calculate a property associated with at least one of the components of the sample. As used herein the terms analyte(s), compound(s) and component(s) refer to any separable components of a mixture.

According to embodiments, a method chromatographic analysis of a sample containing a plurality of components is provided. The method includes introducing a mobile phase into a fluid flow path, injecting a sample into the flow path at a location downstream from the location of mobile phase introduction, detecting a property of the fluid in the flow path with a first detector at a location on the flow path downstream of the location of injecting the sample thereby generating first measurement data. The mobile phase and sample flow through a first column located downstream of the first detector. A second detector is used to detect a property of fluid in the flow path at a location downstream of the first column thereby generating second measurement data. A property associated with at least one of the components of the sample is calculated by at least combining the first measurement data and the second measurement data.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3 shows a simple single-dimension chromatography system with an additional detector, according to embodiments;

FIG. 4 shows a single-dimension chromatography system with two additional detectors, according to embodiments;

FIG. 5 shows a 2-dimensional separation system according to embodiments; and

FIG. 6 shows an additional detector on the vent line of a split-injection system according to embodiment.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The use of non-destructive detectors (i.e. detectors that do not destroy or modify the sample) in multiple locations throughout the flow path of a chromatograph (gas, liquid, etc) or other dynamic separation system is described herein. Traditionally, detectors are placed only at the end of such systems to detect eluting analytes. Generally, detectors are destructive (destroy or modify sample), expensive, have large internal dead volumes, any may require a makeup flow (inert mobile phase); also data acquisition bandwidth on control boards is usually limited. Therefore it has not been generally a high priority for the typical chromatographer to consider multiple detectors within a single chromatographic flow path. However, with modern advances in micro- and nano-technologies, a variety of chromatographic detectors are possible that can be placed along the sample flow path without modifying the sample or causing significant band broadening (e.g. thermal conductivity detectors, microsensors, microsensor arrays, etc.). Several useful applications are made possible by providing additional detectors as described herein. First of all, the diagnosis of many typical problems can be simplified by including these additional detectors. These diagnoses are of critical importance when considering micro-fabricated chromatographic systems with non-ideal flow paths and/or conditions. Second, new quantitative methods are possible by comparing peak areas at different stages of the system flow path. Third, by continuously comparing detector outputs (i.e. subtracting or dividing), new types of signals can be generated.

Figure 1:
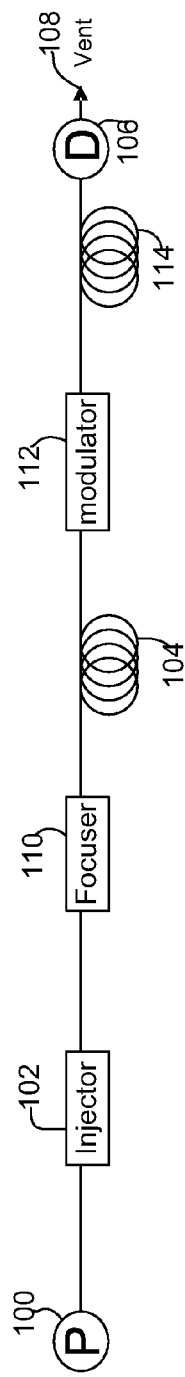
FIG. 1 shows the configuration of a typical conventional gas chromatography system.
Figure 2:
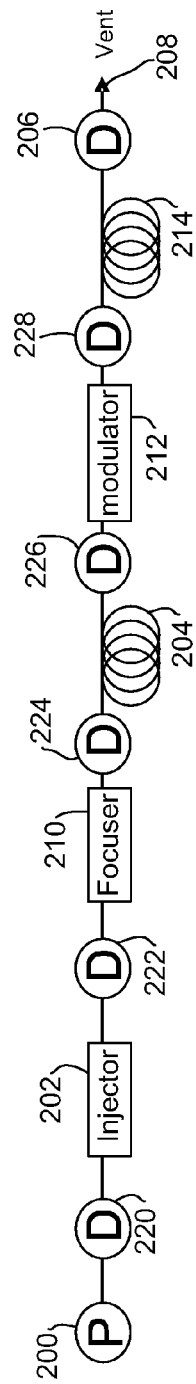
FIG. 2 shows a multi-dimensional chromatographic system having multiple detectors according to embodiments.

FIG. 2 shows a multi-dimensional chromatographic system having multiple detectors according to embodiments. The system is similar to that shown in FIG. 1 in that it includes a pressure source 200, injector 202, a focuser 210, a column 204, a modulator 212, second column 214, detector 206 and vent 208. According to embodiments, additional detectors 220, 222, 224, 226 and 228 are provided. Each of the detectors 220, 222, 224, 226 and 228 preferably has several qualifications. First of all, it should be non-destructive; it should not destroy a significant amount of the sample, and should modify the sample as little as possible. Second, it should be of low dead volume so that it does not cause significant band broadening of analytes passing through the device. Third, it should be either heated and/or fabricated from an inert material, such that no significant sorptive (retentive) interactions occur between the analyte and the detector. A detailed explanation of the advantages of having each of the detectors 220, 222, 224, 226 and 228 will now be discussed.

A detector in the location of detector 220 of FIG. 2 is preferably not exposed to the sample. Therefore, assuming all detectors in the system are similar and calibrated in the same way, detector 220 will provide a representative background based on the current system flow conditions and mobile phase purity. In many cases, an analog circuit can be referenced the output of detector 220 to provide a built-in baseline subtraction amplification. Also, if detector 220 is a thermal conductivity detector (TCD), which is used for gas chromatography (GC), detector 220 can be used to determine the flow rate of the carrier gas. Although, flows may vary within the system due to pressure restrictions, knowing the flow at one point can be the basis for an estimate the flow at other points in the system with a fair degree of certainty.

A detector in the location of detector 222 is only be exposed to the sample immediately after injection. Therefore, detector 222 can serve as a diagnostic tool for monitoring the injection characteristics such as injection plug width. Detector 222 also can perform the same duties as a detector 220 once the injection plug has passed, which provides a second diagnostic capability. Mobile phase impurities are often introduced by residual contamination of the injector 202. Therefore, a different baseline between detector 220 and detector 222 would be a clear identifier of this situation.

A detector in the location of detector 224 functions similarly to one in the location of detector 222, although in this case detector 224 is capable of diagnosing the focuser module 210 rather than the injector 202. Again, a difference in baseline between a detector 222 and detector 224 is an indication of contamination from the focuser 210. Also, the purpose of focuser 210 is to sharpen the peaks from the injector, so by comparing the peak shape of detector 222 and detector 224, monitoring the performance of focuser is provided.

A detector in the location of detector 226 has several unique advantages. First of all, it directly monitors the output of the first column 204. For many systems, this may be the end of the flow path, so this would be the equivalent of the traditional detector. However, for multicolumn systems or 2D GCs, this location is the entry point to the modulator 212. In many 2D-GC systems the modulator 212 requires a large amount of power and usually adds analysis time to the cycle. By monitoring what is going into the modulator 212, the modulation cycle can be modified or even turned off to optimize the use of power and time. In some cases, the detector 226 may provide chemical selectivity, such that it can also identify or classify analytes. In this case, the detector 226 would also provide a means of mapping the flow path of certain compounds through the system. This could potentially eliminate the need for a modulator 212, and open up even more complex chromatographic methods such as 3D GC or as many unique dimensions are available.

A detector in the location of detector 228 provides diagnostics for the modulator 212 in much the same way as detectors 222 and 224 would for the injector 202 and focuser 210. One additional function of a detector 228 is to monitor the peak shape of the modulator output, especially for the case of a selective detector that provides the ability to identify vapors. For many compounds, the output profile from the modulator 212 may be unique to the chemistry between each analyte and the inner-surfaces of the modulator 212, and therefore may contribute additional information that will help in identifying unknown compounds.

Detectors can also be located on system vents. Vents are often used as part of a split injection, modulation system, or flow adjustor system. A common problem with split injections is that the split ratio may vary slightly from day to day, and therefore an internal standard is often used to estimate the split ratio. By monitoring the sample fraction that exits through the split vent, the split ratio can be determined accurately and precisely without the need to "spike" the sample with an internal standard. Also, many diagnostic functions can be performed. For example, detectors on septum purge and inlet purge lines will indicate whether the exhausts are actually venting contamination. This will indicate contamination problems quickly and allow for advanced power, gas, and time saving features (i.e. turn off the septum purge if it is not necessary).

Different non-destructive detectors can also be placed in series or in parallel. Some detectors may have different strengths and weaknesses, therefore multiple detectors in series or parallel may provide more analyte information. In addition, composite signals (i.e. signals from multiple detectors that are subtracted, added, multiplied, or divided with one another) may provide more direct means of measuring sample properties based on differences in detector selectivity.

FIG. 3 shows a simple single-dimension chromatography system with an additional detector, according to embodiments. The system of FIG. 3 includes pressure source 300, flowline 342, injector 302, detector 322, column 304, detector 306 and vent 308. Also shown is data storage 312 that records and stores measurement data from detectors 322 and 306, and processor 310 which is programmed to process data from detectors 322 and 306. Data storage 312 and processor 310 can be part of a general purpose computer, a network of computers, or a dedicated special purpose processor and storage, depending on the particular application. Data storage 312 and processor 310 can also be either co-located with the other system elements shown in FIG. 3, or can be locate remotely. The measurement data from detectors 322 and 306 can be transmitted to data storage 312 directly via an I/O interface (not shown), can be sent indirectly for example via an intermediate storage system (not shown). Although a processor and data storage are not shown in FIGS. 2 and 4-6, it is understood that similar facilities are provided for storing and processing data from the detectors shown in those figures.

The system shown in FIG. 3 is useful for many traditional separation applications, while providing improved long-term durability by virtue of detector 322. First, this added detector provides a measurement of the injection pulse width from injector 302, which is useful in diagnosing injection problems as well as monitoring changes in injection with various samples (injection width is often sample dependent). Secondly, additional quantitative strategies can be employed, for example, the peak area of the injection as measured with detector 322 can be compared to the total peak area of all eluted components as seen by detector 306. The difference, assuming that the detectors are otherwise identical, is that due to compounds that have not eluted from the column. In some cases, those components may not be of importance, and therefore this is simply a measure of column contamination and can be used to recommend column cleaning (baking, washing, etc) or replacement. For example, in the arrangement of FIG. 3, processor 310 is used to compare peak area data from detector 322 with the sum of data from the corresponding peak areas from detector 306 to determine how much of the sample is still retained on column 304. If the contaminating components are known and their effects characterized, this measure of column contamination could be used to correct for changes in retention times due to the contamination acting as additional stationary phase or competitive sorption between the contamination and other analytical components.

In compositional analysis methods, such as used in the oil industry for equation of state modeling, the relative mass fraction of each separated component is often of interest. However, in the case of un-eluted components, an error is created for compounds of unknown concentration, which is often called the "plus fraction." By measuring the peak area of the injection plug, and using this for the denominator in mass-fraction calculations (rather than the sum of the eluted peak areas), some "plus fraction" related errors can be avoided. For example, in the arrangement of FIG. 3, processor 310 is used to divide the areas of each peak detected by detector 306 by the single peak area detected by detector 322, thereby a yielding a more accurate mass fraction calculation. Subtracting the total of peak areas detected by detector 306 from the single peak area detected by detector 322 all divided by the single peak area detected by detector 322 yields a more accurate measure of the plus-fraction.

FIG. 4 shows a single-dimension chromatography system with two additional detectors, according to embodiments. The system of FIG. 4 is similar system to that of FIG. 3, but with an added detector 430 at the end of the system. The rest of the system includes pressure source 400, injector 402, detector 422, column 404, detector 406 and vent 408. A preferred use of the system shown in FIG. 4 is to use non-destructive detectors as detector 422 and detector 406, and a selective detector as detector 430. By comparing the measured chromatograms of detectors 406 and 430, the identification of eluted components is improved. For example, according to an embodiment, the system in FIG. 4 is a gas chromatograph, detectors 422 and 406 are TCD type detectors, and detector 430 is a Nitrogen Phosphorus Detector. In this embodiment, detector 406 shows a chromatogram with all eluted components being detected, while detector 430 only shows nitrogen and phosphorus containing components. By comparing these two chromatograms, the non-nitrogen and non-phosphorus components are discerned. Other detectors that could be used in this embodiment for detector 430 include a flame ionization detector (FID), electron capture device (ECD), photoionization detector (PID), ion mobility spectrometer (IMS), differential mobility spectrometer (DMS), and a mass spectrometer (MS).

FIG. 5 shows a 2-dimensional separation system according to embodiments. The system of FIG. 5 includes a pressure source 500, injector 502, detector 522, a first column 504, a detector 526, a modulator 512, detector 528, a second column 514, detector 506 and vent 508. Detector 522 is working in the same fashion as detector 322 described above in conjunction with FIG. 3. Detectors 526 and 528 are measuring the input and output of the modulator 512. Detector 526 can allow for "smart modulation," that is to only cycle the modulator when it is "loaded" with eluted components from column 504. Doing this saves time and energy during the separation, which is especially valuable in remote system applications. Detector 528 serves a similar function to detector 522 in that it monitors the output of the modulator 512. Subtracting total peak areas measured with detector 506 from the input pulses on detector 528 will give you a measure of what has not eluted from column 514, just as subtracting the total peak areas from detector 526 from the injection pulses measured from detector 522 will give you a measure of what has not eluted from column 504. Comparing detectors 528 and 526 in the same way will also give you a measure of what has not been released from the modulator 512.

FIG. 6 shows an additional detector on the vent line of a split-injection system according to embodiment. The system of FIG. 6 is a 1-dimensional separation system which includes pressure source 600, injector 602, detector 622, column 604, detector 606 and vent 608. Also included is vent line 640 leading to detector 632, flow restrictor and/or metering valve 634, and vent 636. Split-injection systems are widely used, and are plagued by slight fluctuations in split ratio which lead to quantitative errors in sample analysis. Typically an internal standard is added to the sample to alleviate as much error as possible. However, "spiking" samples with internal standard can be incredibly difficult, especially in remote system applications. The peak area of detector 632 during a sample injection will be related to the mass of sample that was vented. Detectors 622 and 606 give measures of the sample that was injected. The ratios of the total peak areas allow direct calculation of the split ratio of the injection system. This is of considerable value as it can allow the use of methods that do not contain an internal sample.

As mentioned above, in selecting suitable detectors there are several important considerations. The detector should be non-destructive; it should not destroy, and should modify the sample as little as possible. The detector should be of low dead volume so that it does not cause significant band broadening of analytes passing through the device. Finally, the detector should be either heated and/or fabricated from an inert material, such that no significant sorptive (retentive) interactions occur between the analyte and the detector. Several methods and techniques have been propose that could be used for the purposes described herein. For example, see: D. Cruza, J. P. Chang, S. K. Showalter, F. Gelbard, R. P. Manginell and M. G. Blain, *Sensors and Actuators*, B: Chemical, Volume 121, Issue 2, 20 Feb. 2007, Pages 414-422; Chen, K., Wu, Y.-E., *Thermal analysis and simulation of the microchannel flow in miniature thermal conductivity detectors* (2000), Sensors and Actuators, A: Physical, 79 (3), pp. 211-218; Gajda, M. A., Ahmed, H., *Applications of thermal silicon sensors on membranes*, (1995) Sensors and Actuators, A: Physical, 49 (1-2), pp. 1-9; Kimura, Mitsuteru, Manaka, Junji, Satoh, Shigemasa, Takano, Shigeki, Igarashi, Norikazu, Nagai, Kazutoshi, *Application of the air-bridge microheater to gas detection* (1995) Sensors and Actuators, B: Chemical, B25 (1-3 pt 2), pp. 857-860; Laugere, F., Lubking, G. W., Berthold, A., Bastemeijer, J., Vellekoop, M. J., *Downscaling aspects of a conductivity detector for application in on-chip capillary electrophoresis* (2001) Sensors and Actuators, A: Physical, 92 (1-3), pp. 109-114; Simon, I., Arndt, M., *Thermal and gas-sensing properties of a micromachined thermal conductivity sensor for the detection of hydrogen in automotive applications* (2002) Sensors and Actuators, A: Physical, 97-98, pp. 104-108; Sorge, S., Pechstein, T., *Fully integrated thermal conductivity sensor for gas chromatography without dead volume*, (1997) Sensors and Actuators, A: Physical, 63 (3), pp. 191-195; Wu, Y. E., Chen, K., Chen, C. W., Hsu, K. H., *Fabrication and characterization of thermal conductivity detectors (TCDs) of different flow channel and heater designs* (2002) Sensors and Actuators, A: Physical, 100 (1), pp. 37-45; U.S. Pat. No. 5,756,878; and U.S. Pat. No. 4,909,078, all of which are incorporated herein by reference.

Additionally there is at least one TCD that can currently be obtained commercially from C2V which supplies Microsystems solutions from Concept to Volume, based in the Netherlands. It has been found that the micro TCD from C2V is suitable for many of the applications described herein.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while some of the embodiments described herein refer to gas chromatography, the present invention is also applicable to other types of chromatographic analysis such as liquid chromatography and supercritical fluid chromatography. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for chromatographic analysis of a sample containing a plurality of components, the system comprising:
    a pressurized source of a mobile phase;
    a flow path in fluid communication with the pressurized source such that the mobile phase flows through the flow path;
    an injector in fluid communication with the flow path and downstream of the pressurized source, the injector configured to inject the sample into the flow path;
    a first column containing a stationary phase and forming part of the flow path, the first column being located downstream of the injector;
    a first detector in fluid communication with the flow path, and positioned to detect properties of fluid in the flow path at a location downstream of the injector and upstream from the first column;
    a second detector in fluid communication with flow path, and positioned to detect properties of fluid in the flow path at a location downstream of the first column; and
    a processor configured to receive first peak measurement data from the first detector and second measurement data from the second detector and combine the first and second peak measurement data to calculate a property associated with at least one of the components of the sample.

2. A system according to claim 1, wherein the first detector is designed and arranged such that a substantial portion of the sample remains in the flow path after the first detector is operated.

3. A system according to claim 1, wherein the first detector is designed and arranged such that no significant sorptive interactions occur between the sample and the first detector.

4. A system according to claim 1, wherein the first detector is designed and arranged such that it does not cause significant band broadening of sample compounds as they pass through the first detector.

5. A system according to claim 1, further comprising a third detector in fluid communication with flow path at a location downstream of the second detector, wherein the second detector and third detector are of different types thereby complementing the sensing capabilities of each other.

6. A system according to claim 1, further comprising:
    a second column containing a second stationary phase and forming part of the flow path and being located downstream of the first column; and
    a third detector in fluid communication with the flow path and located downstream of the first column and upstream of the second column.

7. A system according to claim 6, further comprising:
a modulator in fluid communication with the flow path at a location be downstream of the third detector and upstream of the second column; and
a fourth detector in fluid communication with the flow path and located downstream of the modulator and upstream of the second column.

8. A system according to claim 1, further comprising:
a focuser in fluid communication with the flow path at a location downstream of the first detector and upstream of the first column; and
a third detector in fluid communication with the flow path at a location downstream of the focuser.

9. A system according to claim 1, further comprising:
a vent line in fluid communication with the flow path at a location downstream of the detector and upstream of the first column;
a vent in fluid communication with the vent line at a location on the vent line downstream of the location of fluid communication of the vent line and the flow path; and
a third detector in fluid communication with the vent line at a location up stream from the vent and downstream of the location of fluid communication of the vent line and the flow path.

10. A system according to claim 1, wherein the system is a gas chromatography system.

11. A system according to claim 1, wherein the system is of a type selected from the group consisting of: liquid chromatography and super critical fluid chromatography.

12. A system according to claim 1, wherein the processor is configured to calculate from the first measurement data an area of a peak associated with the plurality of components of the sample and to calculate from the second measurement data a sum of areas of peaks wherein each peak is associated with one of the plurality of components, and to compare the peak area from the first measurement data with the sum of peak areas from the second measurement data to calculate an estimate of how much of the sample is retained by the first column.

13. A system according to claim 1, wherein the processor is configured to calculate from the second measurement data an area for a peak associated with one of the plurality of components and calculate from the first measurement data an area for a peak associated with the plurality of components, and to calculate therefrom a mass fraction associated with the one of the plurality of the components.

14. A system according to claim 1, wherein the processor is configured to calculate from the first measurement data an area of a peak associated with the plurality of components of the sample and to calculate from the second measurement data a sum of areas of peaks wherein each peak is associated with one of the plurality of components, and to calculate therefrom a measure of the plus-fraction.

* * * * *